United States Patent [19]

Cheminal et al.

[11] 4,248,673
[45] Feb. 3, 1981

[54] PROCESS FOR OBTAINING COLORLESS AND STABLE ISOPHORONE

[75] Inventors: Bernard Cheminal, La Chambre; Paul Kiener, St. Genis Laval, both of France

[73] Assignee: Produits Chimiques Ugine Kuhlmann, Courevoie, France

[21] Appl. No.: 7,695

[22] Filed: Jan. 30, 1979

[30] Foreign Application Priority Data

Feb. 7, 1978 [FR] France .................... 78 03352
Dec. 8, 1978 [FR] France .................... 78 34579

[51] Int. Cl.$^3$ ............................... B01D 3/34
[52] U.S. Cl. ........................... 203/35; 203/37; 210/664; 568/376
[58] Field of Search .............. 203/28, 29, 31, 32, 203/33, 41, 35, 34, 37; 210/26; 260/586 R, 586 P, 586 C, 586 M

[56] References Cited

U.S. PATENT DOCUMENTS

3,462,348  8/1969  Wellman et al. ............. 260/586 C
3,652,407  3/1972  Paleos ............................ 210/40

*Primary Examiner*—Frank Sever
*Attorney, Agent, or Firm*—Pennie & Edmonds

[57] ABSTRACT

A process for obtaining colorless and stable isophorone is characterized by distilling a raw synthesis mixture to remove alkaline agents, acetone, and a major portion of the water which is present, thermally treating the distilled mixture with an acidic ion-exchanging resin, neutralizing the effluent following said thermal treatment with an excess of an alkaline agent, adding water in a volume sufficient to dissolve any salts which may have formed, then again, neutralizing the now alkaline mixture wherein the pH of the resultant mixture is between 6.5 and 7, washing the mixture in water by decantation, and distilling the mixture under reduced pressure.

10 Claims, 3 Drawing Figures

PROCESS FOR OBTAINING COLORLESS AND STABLE ISOPHORONE

TECHNICAL FIELD

The present invention relates to a process for obtaining a colorless, nonacid isophorone. The process comprises treating colored isophorone with ion-exchanging resins, neutralizing the isophorone mixture extracting salts with water, and distilling the washed isophorone mixture.

BACKGROUND ART

The preparation of isophorone by alkaline condensation of acetone at a high temperature and under pressure is well known. In addition to producing isophorone by alkaline condensation, the process produces certain secondary products as well. Some secondary products, such as mesityl oxide, may be easily eliminated by distillation. Other products, however, particularly those which are only slightly more volatile than isophorone, are separated only with difficulty, if at all. This is the case even using distilling columns with a high degree of separating power.

The presence of secondary products in industrial isophorone is particularly undesirable. Some secondary products have a strong yellow coloring which militates against the production of colorless commercial grade isophorne. Further, these secondary products accelerate a new progressive coloring of isophorone. Also, the secondary products may increase the acidity of stored isophorone by oxidation.

French Pat. No. 1,205,799 describes treating dry, colored isophorone with an aromatic sulfonic acid at a temperature falling between 80° C. and 160° C. The isophorone is then separated from the resulting mixture by distillation. This process has several drawbacks. The added sulfonic acid is wasted upon being eliminated with the distillation residues. Furthermore, the presence of sulfonic acid enhances the degradation of the isophorone during the treatment. Another disadvantage is the corrosion phenomena which is inevitable whenever steel is employed in the process.

French Pat. No. 1,215,326 describes a process for obtaining colorless isophorone by treating isophorone with fuller's earth, a natural product belonging to the group of aluminum silicates known as montmorillonites. As is the case with several natural products, the characteristics of fuller's earth are subject to variation. Accordingly it is dangerous to prepare an industrial product like isophorone with this unconstant auxiliary product.

Thus, a process which eliminates the problems and overcomes the disadvantages of the prior art as well as to obtain a stable colorless product is of great value.

DISCLOSURE OF INVENTION

In accordance with the present invention, a raw synthesis mixture containing an isophorone product is partially purified. The purification process results in the removal of the following compounds by distillation: untransformed acetone, a greater part of the water of reaction, an alkaline agent, which is a condensation catalyst. The distilled isophorone mixture is then thermally treated by means of an acidic ion-exchange resin. The thermal and catalytic treatment transforms the unwanted colored impurities into nonvolatile compounds. The effluent from the ion exchange step is subjected to a neutralization agent present in an amount slightly in excess of that amount to ensure a complete neutralization of any effluent acidity.

That level of alkalinity introduced by the excess neutralization process must be neutralized. The removal of alkaline agents from the isophorone mixture is necessary since their presence can result in polymerization phenomena if a direct distillation of the mixture was attempted. Therefore, the mixture is neutralized a second time. This second neutralization, however, results in the isphorone mixture having a pH between 6.5 and 7. To eliminate the salts which are formed as a result of the neutralization, the mixture is then washed with water by decantation. Finally, colorless and stable isophorone is obtained by distilling the washed, neutral mixture under reduced pressure.

Thus, the process of the invention overcomes the various disadvantages of the prior art and the product obtained is a colorless and non acidic isophorone derived from perfectly defined industrial products. This isophorone product is desirable in that it retains a high quality during a long period of storage.

In the preparation of partially purified isophorone mixtures by the present process, it is also possible to eliminate certain compounds which are less volatile than isophorone. One group of compounds which are less volatile than isophorone is the group known as xylithones. An isophorone mixture treated in this manner will be characterized as a "tailed isophorone".

Another preparation of the partially purified isophorone mixture entails a separation of isophorone by distillation which is both as quantitative and qualitative as possible. The removed compounds may be advantageously recycled into a catalysis reactor. This is especially important where there is a danger of the compounds being reduced to unusable compounds, in-passing over an ion-exchaging resin. Furthermore, a maximum elimination reduces the volume of isophorone mixture to be treated. By concentrating the coloring impurities, their transformation to a non-volatile state is better ensured. A tailed isophorone mixture is partially purified as to less volatile compounds is referred to as "tailed and topped" isophorone. Contact between the isophorone mixture and the acid sites of the ion exchange resin can be impeded by the presence of too large a quantity of water. Therefore, it is more advantageous to utilize mixtures which contain less than 1% water, preferably about 0.1% to 0.3%. These relatively anhydrous mixtures can be obtained by heteroazeotropic distillation, the water being eliminated. Mixtures dried in this way are referred to as "tailed, topped and dried" isophorone.

BEST MODE FOR CARRYING OUT THE INVENTION

Ion-exchange resins permit the transformation of compounds having a volatility close to that of isophorone into less volatile compounds. Such a transformation affords an easier separation of the undesirable secondary products from the isophorone. These resins are strongly acidic, macromolecular, reticulated organic compounds. Certain molecules of the constituent monomers bear substituents of a strongly acid nature, such as the —$SO_3H$ group. The support polymers of these groups are phenol-formol or styrene-divinylbenzene copolymers.

A certain number of these ion-exchanging resins are called "macroporous" because of the method of preparation. Preferably, macroporous resins are used in the instant process. One such resin which has been used successfully is sold under the tradename "Amberlyst 15", although the invention may be practiced with other macroporous resins having similar characteristics. "Amberlyst 15" is a registered trademark of the Rohm and Haas Company, France.

The ion exchange resins are manufactured in the form of small balls whose diameter is within the range of between about 0.3–0.4 mm and about 1.2–1.5 mm. The apparent average diameter is approximately 0.5 mm to 0.7 mm. Due to the manufacturing process, the balls have a high degree of porosity which may be approximately 25% to 45%. These macropores possess a diameter of greater than 100 Å. The resins also have a specific surface which is greater than 10 $m^2/g$ and may be as large as 50 $m^2/g$. Finally, their exchange capacity is between 4 and 5 milliequivalents/g. It should be noted that previous values are given for resins in the dry state.

The granulometric distribution of "Amberlyst 15" is as follows:
Diameter greater than 1.2 mm: 2.4%
Diameter between 0.8 and 1.2 mm: 24.2%
Diameter between 0.6 and 0.8 mm: 47.9%
Diameter between 0.4 and 0.6 mm: 18.8%
Diameter between 0.3 and 0.4 mm: 5.7%
Diameter between 0.3 mm: less than 1%
The above distribution results in a porosity of from about 30% to 35%. The specific surface is between 40 $m^2/g$ to 50 $m^2/g$, with macropores with an average diameter falling between 200 Å and 600 Å. Finally, the exchange capacity of this resin is 4.9 milliequivalents.

Certain ion-exchanging resins, i.e. "Amberlyst 15", are delivered in the dry state and may be used in accordance with the present invention without previous treatment. Others, however, are delivered saturated in water. In this case the saturated resins require to be dried prior to use according to the instructions of the manufacturer. A drying method particularly adapted to the present invention involves a heteroazeotropic distillation wherein isophorone is the azeotropic agent.

A minimum temperature of 80° C. is necessary for thermally treating the distilled mixture by means of an ion-exchange resin. The preferable temperature is one where the accompanying secondary products are transformed to non volatile compounds. On the other hand, the maximum temperature for thermal and catalytic resin treatment may not exceed the temperature at which the ion-exchanging resins commence to lose their stability, a temperature of about 120° C. Thus a useful temperature range varies from 100° C. to 115° C.

The process of the invention can be used in various ways. For example, isophorone may be treated in a discontinuous manner. Thus a quantity of isophorone may be reacted for a given period of time with a specific quantity of resin while the isophorone is repeatedly circulated over a bed of the ion-exchange resin.

It is also possible to treat isophorone in a continuous manner according to the invention. In a continuous process isophorone only traverses the bed of ion-exchanging resin once. The exposure period is defined by the ratio of volume of resin isophorone output. Thus, the exposure period lasts between 30 minutes and 4 hours, and preferably between 1 hour and 2 hours.

A thermal discoloration treatment may be combined with the elimination of secondary products in the continuous process. Both the elimination step and the isolation of colorless isophorone are carried out by distillation under reduced pressure, in accordance with the known prior art techniques.

The effluent from the discoloration, ion-exchange reactor usually contains at least one substance which is acidic and slightly more volatile than isophorone. Precautions should be taken so that the colorless isophorone will be free of these destabilizing compounds, after being isolated.

The applicant has observed that the acidity present in the reactor effluent diminishes in conformity with the aging of the resin. Correspondingly, a decrease in the acidity of the isophorone product is obtained. The lowering of the acidity, however, is neither large nor rapid enough to make a directly distilled isophorone product having good quality.

Various precautions can be taken in order to obtain a commercially acceptable and stable product. As a non-limiting example, the effluent of the discoloration reactor may be subjected to a fractionated rectification in which a very acidic top fraction may be removed and recycled in the synthesis reaction. This option affords acid removal in a continuous manner.

The above measures are not entirely satisfactory due to a loss of productivity. Specifically, the production of isophorone would entail a further processing step. Additionally, the reprocessing options are expensive with regard to energy consumption.

It is possible to mitigate the above disadvantages by performing an extraction of the acid substances present in the crude effluent from the resin reactor. The extraction is accomplished by means of a series of solvent washings. As known by those skilled in the art, the effluent is insoluble in the solvent, yet the acid substances are easily soluble therein. Water is the preferred solvent.

This procedure is not entirely practical in that a considerable number of stages of extraction are required. Furthermore, the solvent washings create an extracted loss of a portion of the isophorone product. On the other hand, the acidity of the isophorone product prior to aging, is approximately 0.004% expressed in acetic acid.

In treating the effluent from the thermal and catalytic treatment, the present invention is not subject to the disadvantages of the prior art. The present invention is characterized by neutralizing the acidity present in the effluent, extracting the salts formed by means of a water washing and isolating the commercial isophorone by rectification.

The neutralization of the acidity present in the effluent of the discoloration reactor should be complete.

Therefore, a slight excess of an alkaline agent is employed. Soda may be used. A 15% stoichiometric excess of the alkaline agent is preferred.

In practice, this neutralization is carried out by means of an agitated, aqueous solution of sodium hydroxide. For the neutralization to be effective, it is necessary for the neutralized mixture to remain homogeneous. Thus, the quantity of water to be introduced for extracting the formed salts is limited to the minimum amount which will dissolve the isophorone. For example 3.5% water at 80° C. Typically this requirement results in a soda concentration between about 10 g/l and 30 g/l.

The temperature for the neutralization step is not critical. A slight cooling of the reactor effluent, i.e. 80° C., prior to introducing the aqueous solution of sodium hydroxide is sufficient. Lower operating temperatures are permissible.

If direct distillation of the alkaline mixture were performed, there would be a danger of causing isophorone polymerization phenomena. Therefore, the excess of soda is neutralized by the addition of an aqueous solution of phosphoric acid. The agitated acid solution has a concentration of 10 g/l. The acid solution is added until the pH of the mixture obtained by the addition of 25 ml of a sample from the final reactive medium to 100 ml of a hydromethanolic solution 50% by volume falls between 6.5 and 7. The temperature for the acid addition is not critical. Typically the range will be between 80° C. and the ambient temperature.

Sodium salts which are formed during the various neutralization processes must be eliminated from the medium. Conveniently, the sodium salts are eliminated by means of water addition. The added water should be sufficient to dissolve the salts which are present but not of such volume to dissolve excess isophorone. To this end, water will dissolve about 2% by its weight of isophorone. Any dissolved isophorone must be recovered. The volume of water used per volume of organic product should fall between 0.2 and 1. Practically, this ratio is close to 0.25.

The dissolving of the salts is facilitated by agitating the mixture, which then is separated. The aqueous phase is immediately parred into a stripping column to recover the isophorone which is dissolved.

A heteroazeotropic distillation permits immediate water elimination in a continuous manner. Water is eliminated at the head of the distilling column without previous topping. Finally a colorless and nonacid commercial isophorone is recovered as the product of a subsequent distillation of the liquid which is removed from the bottom of this drying column.

The following examples are given for the purpose of illustrating the invention and to demonstrate ways of carrying out the invention in a non-limitative manner. The coloring of the isophorone is measured in a Lovibond 100 colorimeter and expressed in Hazen units. (Platinum-cobalt scale according to the ASTM D 1209.62 standard).

EXAMPLE 1

1,000 ml. of tailed isophorone dried by azeotropic distillation is introduced into a glass reactor having a capacity of 1-liter. The reactor is equipped with an agitator and an ascending cooling means. The reactor contains 150 ml of "Amberlyst 15" ion-exchanging resin in the acidic or H+ form. The resin is washed three times with methanol and, thereafter, once with a colored isophorone. The coloring in the isophorone mixture is derived from compounds which are more volatile than isophorone, particularly compounds having a strong yellow color.

The mixture is heated to about 102° C. A darkening of the reactive mass, observed rather rapidly, is characterized of the transformation of the colored impurities.

At the end of 7 hours, the reactive mixture is separated from the resin and distilled under reduced pressure.

A top fraction of 100 ml is taken as a sample. The sample contains 80% of isophorone and it has a coloring of 8 Hazen units. A second fraction of 700 ml is then taken as a sample. The coloring of this sample is between 5 and 8 Hazen units. The temperature at the head of the column is raised. The fraction then obtained has a strong yellow color. This is caused by compounds which are less volatile than isophorone. A sample distillation carried out on the original isophorone without previous treatment makes it possible to collect a core fraction having a coloring of 65 Hazen units.

EXAMPLE 2

Figure 1:
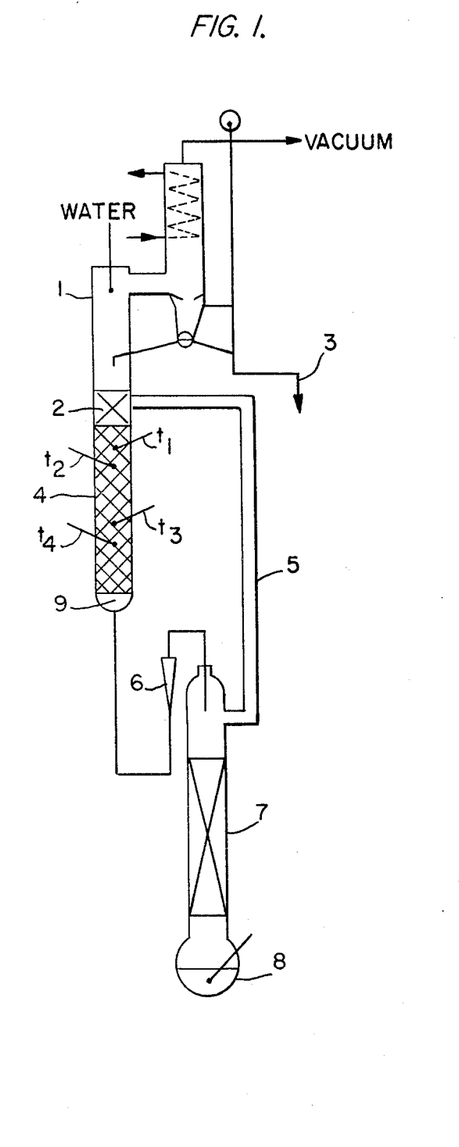
FIG. 1 is a schematic diagram of a reactor bed and a split distillation column wherein the column head is manually controlled.

The isophorone treatment is accomplished by the apparatus of FIG. 1. The apparatus is constucted of borosilicated glass and is sold commercially by the EIVS Company. The apparatus includes a distillation balloon flask (8) having a capacity of 5 liters, and a distillation column (7) on top of the flask. The distillation column is of a length of 1 meter and has a nominal diameter of 50 mm. The column is filled with 6 "Multiknit" knitted, buffers of rustproof steel wire. "Multiknit" is a trademark of the Tissmetal Company. The "Multiknit" fittings may have a diameter of about 50 mm and a length of 15 cm.

A pipe (5) at the top of the column directs the distilled vapors into a "Multiknit" knitted buffer (2) of steel wire and then into the head of column (1). A water-cooled condenser is disposed at the top of the column (1). The internal pressure for the apparatus may be adjusted by means of a vacuum installation.

The head of column (1) or second column is controlled manually. The control permits the separating of heterogeneous mixtures and the sampling of the lower phase of the second column. The samples may be returned by means of routing the sample back to the buffer of the second column. If the distillate is homogeneous, a sample may be taken by means of a pipe (3), without perceptibly changing the working conditions of the apparatus.

The condensed liquid, after passing into the head of the second column and the buffer (2), flows through a bed (4) of an ion-exchanging resin. The bed is of a diameter of 50 mm and has a length of 75 cm. Thermometers, $t_1$ through $t_4$ are disposed along the length of the bed.

A filler (9) and the buffer (2) keep the resin particles in place. The liquid which has passed through the bed of resin returns through a flow meter (6) to the head of the first column (7).

1,400 ml of Amberlyst 15 resin is placed in the bed (4) of the described apparatus and washed with tailed, crude isophorone. Four and two-tenths kilograms of tailed crude isophorone is then introduced into the balloon flask (8).

The first condensate obtained in column (1) is heterogenous. The separated water is eliminated through pipe (3). The apparatus is then put into operation and functions under a pressure of 50 mm. of mercury. The flow rate of distillate is 3.5 liters per hour as measured by flow meter (6).

The following temperatures were noted following 7 hours of operation:

| Temperatures = | head of the column (1) | = 123 (in °C.) |
|---|---|---|
| | at $t_1$ | = 111 |
| | at $t_2$ | = 111 |
| | at $t_3$ | = 91 |
| | at $t_4$ | = 90 |
| | balloon flask (8) | = 131 |

The apparatus is then stopped. The mixture contained in the balloon flask (8) is distilled. The distillate provides 3,700 g. of isophorone having a coloring of 10 Hazen units and 200 g. of isophorone mixed with less volatile or heavy products, fraction which is recyclable in a further distillation.

A distillation was performed on an initial mixture which had not been subjected to the thermal treatment of the present invention. This distillation provides approximately the same quantity of isophorone, but it has a coloring of 65 Hazen units.

EXAMPLES 3 THROUGH 6

Figure 2:
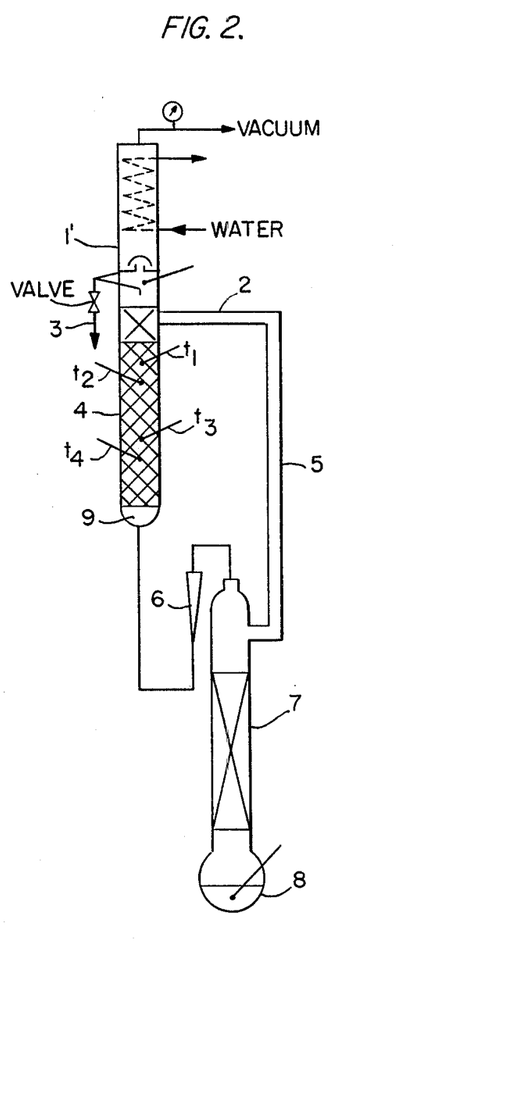
FIG. 2 is a schematic diagram of an apparatus similar to FIG. 1 except that column head has been modified.

The apparatus of Example 2 is modified slightly and may be seen in FIG. 2. As illustrated, the head of the column (1) (see FIG. 1) is replaced by a different head (1') which does not allow for the separation of heterogeneous mixtures. An advantage results from having electronic control over the refluxing rate.

In order to carry out the various examples, the balloon flask (8) is loaded with 4.2 kg of tailed crude isophorone. These mixtures have been dried by azeotropic distillation and partially topped.

The balloon flask is heated, and the apparatus is placed under reduced pressure of approximately 50 mm of mercury. A circulation of isophorone similar to that described in the above example is thereby established.

The flow of liquid passing over the resin, measured by the flow meter (6) is a function of the power provided by a heating system for the balloon flask (8). Circulation of isophorone is achieved while under a reduced pressure of about 50 mm. H.g.

A small sample of the head of the column (1') is taken at regular intervals through pipe (3). The rate of reflux is fixed at 10/1.

The table below indicates the coloring in Hazen units of various samples. The time 0 is taken when the first vapors arrive in the head of the column (1').

| Duration of the reaction | output of liquid (in liters per hour) | | | |
|---|---|---|---|---|
| (in hours) | 1.5 | 3.3 | 5.3 | 9 |
| 1 | | 35 | 35 | 35 |
| 2 | | 12 | 10 | 20 |
| 3 | 30 | 8 | 8 | 17 |
| 4 | | 5 | 5 | 12 |
| 5 | 18 | <5 | <5 | Not measured |
| 6 | | | | |
| 7 | 8 | | | |

Below are the respective temperatures recorded after 5 hours of reaction in the tests. The outputs were 3.3 and 5.3 liters per hour:

| | Temperatues in °C. | |
|---|---|---|
| | Test at 3.3 Liters per hour | Test at 5.3 Liters per hour |
| Head of the column (1') | 121 | 118 |
| at $t_1$ | 114 | 113 |
| at $t_2$ | 112 | 112 |
| at $t_3$ | 93 | 95 |
| at $t_4$ | 92 | 95 |
| Balloon Flask (8) | 132 | 127 |

The initial coloring of the isophorone distilled and taken as a sample at pipe (3) was approximately 60 Hazen units.

The treatment of the present invention is particularly effective in discoloring isophorone. The product to be treated is kept in contact with the ion-exchanging resins for a sufficiently long time.

Also, the stability of the isophorone coloring obtained was verified on the samples taken after 5 hours of reaction wherein the flow rate was 3.3 liters per hour. The samples were under illumination in glass bottles.

The following colorings are recorded in terms of time:

| Time preserved | Untreated Isphorone | Sample in Closed Bottle | Sample in Open Bottle |
|---|---|---|---|
| 0 days | 60 | 5 | 5 |
| 7 days | 80 | 5 | 10 |
| 33 days | Not measurable | 12 | 45 |

EXAMPLE 7

This example illustrates the procedure of the invention in which both the tailed crude isophorone mixture and colorless isophorone are obtained in a continuous manner.

Figure 3:
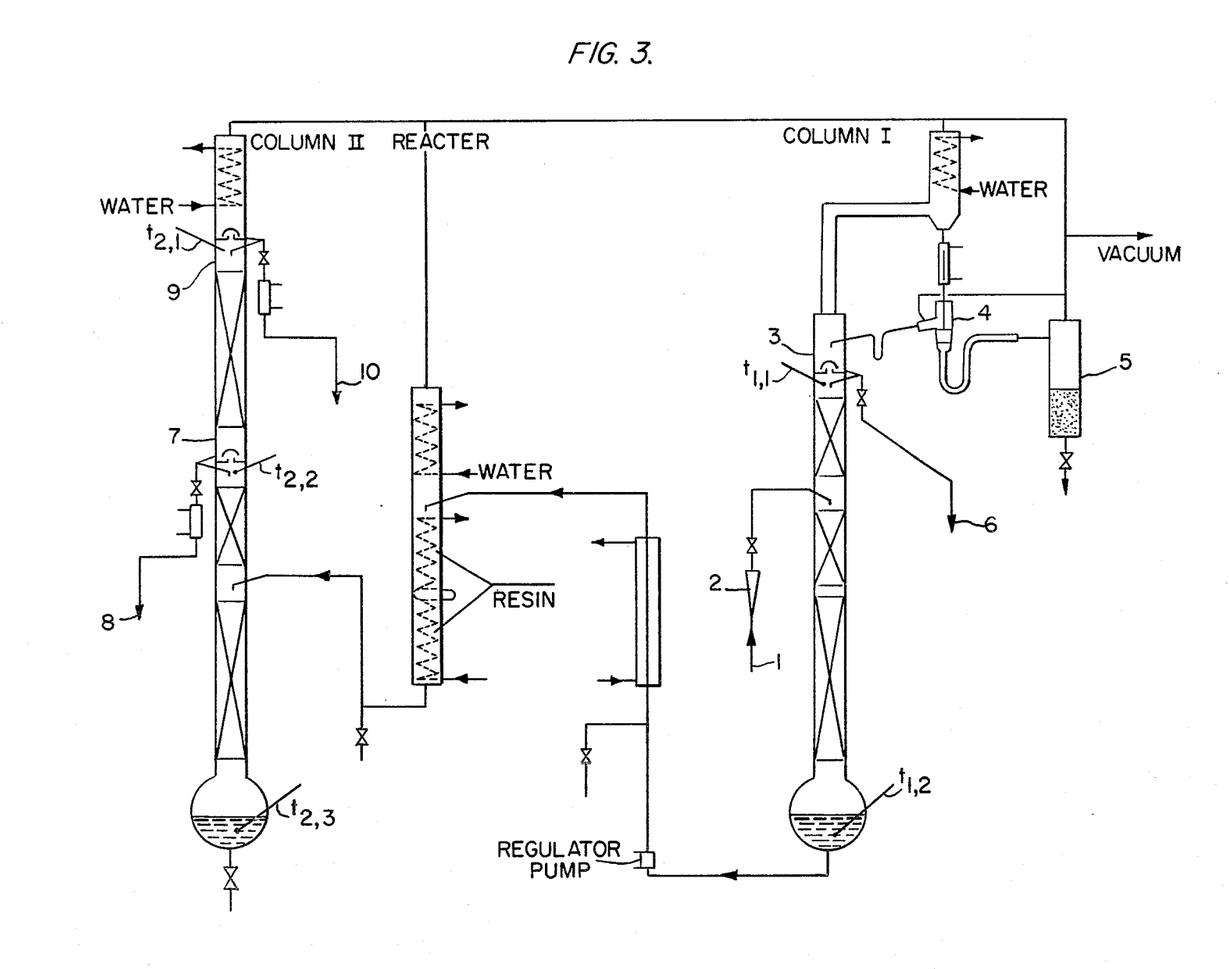
FIG. 3 is a general schematic diagram of a continuous process wherein an isophorone mixture is treated according to the present invention. The process apparatus comprises two distinct distillation columns and an ion-exchange reactor.

The apparatus for this example is illustrated in FIG. 3 and comprises:

I. a continuous distillation column (12);
II. an ion-exchange reactor (14); and
III. a continuous distillation column (16).

The distillation column receives the tailed isophorone to be treated and separes those compounds which are more volatile than is isophorone from the column. The reactor treats the colored impurities, while the distillation column delivers colorless isophorone product and receives effluent from the reactor.

More specifically, the tailed isophorone is introduced to column (12) through pipe (18) and flow meter (20). The tailed isophorone contains about 3% water by weight.

The first column (12) comprises a heated balloon flask having a 10-liter capacity and three sleeves. Each sleeve has an interior diameter of 50 mm and their lengths upwardly from the balloon flask, are 1, 0.5 and 0.5 meter, respectively. The longer sleeve is filled with 6 "Multiknit" buffers. The other sleeves are filled with 2 buffers. A head (22) of the column (12) is identical with those used in Examples 3 through 6, see FIG. 2.

A steam condenser and a condensed vapors separator (24) disposed in upright relation permit the return of the upper organic phase into the head (22). The separator (24) accumulates the lower aqueous phase in a reservoir (25). A pipe (26) connected to the head (22) permits the collection of a fraction of the upper organic phase from separator (24). This fraction consists of isophorone containing more volatile compounds and may be reprocessed in a synthesis reactor.

Thermometers $t_{1,1}$ and $t_{1,2}$ measure the temperatures at the head (22) and in the balloon flask of the column.

Tailed, topped and dried isophorone returns to the balloon flask of column 12. A dosimeter-type pump (28) passes the mixture in the balloon flask through an exchanger-heater in the upper part of the ion-exchange reactor. The mixture is then injected into the reactor. The reactor used here is a glass reservoir with a constant temperature coil. An exchanger cooler intended to condense and reduce any isophorone vapors is located at the top of the reactor (14).

The ion-exchanging resin (1.85 liters of Amberlyst 15 in the acidic form) is placed on the inside of the reactor and kept entirely immersed at the desired reaction temperature by the circulation of the thermostatically controlled, heat-conducting oil through the coil.

The effluent from the reactor feeds the distillation column (16) equipped with a heated balloon flask and 2 sleeves. The balloon flask has a 10-liter capacity and the sleeves are 1 meter and 0.5 meter long. The longer sleeve adjacent the balloon flask contains 6 "Multiknit" buffers. The other sleeve contains 2 "Multiknit" buffers. An inlet for the reactor effluent separates the sleeve network from the top of the column.

A system for taking lateral samples (29) is located above the inlet. This system permits a fraction of the liquid to flow in reflux through pipe (32). The head of the column (30) is equipped with a vapor condenser (31). A fraction of the condensed vapors flow through a pipe (34). This fraction contains acid isophorone which is to be reprocessed in a synthesis reactor. Transformed secondary products being less volatile than isophorone accumulate in the heater. They are eliminated periodically.

Thermometers $t_{(2)1}$, $t_{(2)2}$ and $t_{(2)3}$ give the respective temperatures at the head of the column, in the lateral sample-taking system (29) and at the foot of the column.

Finally, the entire unit consisting of the columns and the reactor is placed under reduced pressure by means of a collector plugged into a vacuum installation.

In the above apparatus, the following operating conditions are applied:

| | |
|---|---|
| Pressure | 45 mm of mercury |
| Output at (20) | 1.25 liters per hour of tailed crude isophorone |
| $t_{(1),1}$ | 80° to 90° C. |
| $t_{(1),2}$ | 129° C. |
| Output at (25) | 35 ml/hr |
| Output at (26) | 25 ml/hr |
| Temperature of reaction | 111° C. |
| $t_{(2),1}$ | 118°-119° C. |
| $t_{(2),2}$ | 121.5° C. |
| $t_{(2),3}$ | 135° C. |
| Rate of reflux at (30) | 24/1 |
| Output at (34) | 70 ml/hr |
| Rate of reflux at (29) | 4/1 |
| Output at (32) | 1,100 ml/hr |

Samples are taken at pipes (32) and (34) once a dynamic equilibrium is established.

The coloring and acidity of the samples are noted with respect to time. In order to establish a shelf life, the samples are subjected to illumination while in open bottles.

| Length of Storage | Isophorone Sample Taken at (32) | | Acid Isophorone Sample Taken at (34) | |
|---|---|---|---|---|
| | Coloring | % Acidity | Coloring | % Acidity |
| 0 days | 5 to 8 | 0.0024 | 5 to 8 | 0.05 |
| 15 days | 12 | 0.0072 | Very strongly colored (70) | 0.1 |
| 37 days | 30 | 0.0096 | — | — |

The isophorone sample taken at pipe (32) slowly colors in an open bottle. Measurement was not taken in a closed bottle since color development would have been much slower. No significant variation in coloring could have been observed. A comparative test was carried out by distilling separately, on an effective distillation column, the crude isophorone being supplied to the installation. It was not possible to obtain fractions having a coloring less than 60.

A standard distillation in accordance with the ASTM D 1078 standard was carried out on a sample taken at (32), too.

The following values, in °C., were obtained:

| ASTM Standard | | Current Commercial Product | Sample Taken at (32) |
|---|---|---|---|
| Initial Point | 205 | 209 | 210 |
| Dry Point | 218 | 217 | 214 |

EXAMPLE 8

In the same apparatus described in Example 7, the following operating conditions are applied:

| | |
|---|---|
| Pressure | 44 mm of mercury |
| Output at (20) | 1.77 liters per hour of tailed crude isophorone |
| $t_{(1),1}$ | 80 to 90° C. |
| $t_{(1),2}$ | 127 to 128° C. |
| Output at (25) | 52 ml/hr |
| Output at (26) | 40 ml/hr |
| Temperature of reaction | 111° C. |
| $t_{(2),1}$ | 118° C. |
| $t_{(2),2}$ | 121.5° C. |
| $t_{(2),3}$ | 135° C. |
| Rate of reflux at (30) | 32/1 |
| Output at (34) | 100 ml/hr |
| Rate of reflux at (29) | 3/1 |
| Output at (32) | 1,640 ml/hr |

Samples were taken at pipes (32) and (34) once a stable operation was achieved. Again the samples preserved in open bottles.

Coloring and acidity were measured regularly in the course of time. The following results were obtained:

| Length of Storage | Isophorone Sample Taken At (32) | | Acid Isophorone Sample Taken at (34) | |
|---|---|---|---|---|
| | Coloring | % Acidity | Coloring | % Acidity |
| 0 days | 6 | 0.002 | 8 | 0.04 |
| 14 days | 12 | 0.005 | Very strongly colored (70) | 0.09 |
| 36 days | 30 | 0.01 | — | — |

A standard distillation carried out on a sample taken at (32) gives the same results as those observed in Example 7.

EXAMPLE 9

In the apparatus used in Examples 7 and 8, one applies the following operating conditions:

| Pressure | 44 mm of mercury |
|---|---|
| Output at (20) | 2.3 liters per hour |
| $t_{(1),1}$ | 80 to 90° C. |
| $t_{(1),2}$ | 128° C. |
| Output at (25) | 70 ml/hr |
| Output at (26) | 45 ml/hr |
| Temperature of reaction | 111° C. |
| $t_{(2),1}$ | 120° C. |
| $t_{(2),2}$ | 123° C. |
| $t_{(2),3}$ | 138° C. |
| Rate of reflux at (30) | 2/1 |
| Output at (34) | 390 ml/hr |
| Rate of reflux at (29) | 1/1 |
| Output at (32) | 1,700 ml/hr |

Samples were taken as before and analyzed. The results are:

|  | Isophorone Sample Taken. at (32) | Acid Isophorone Sample Taken at (34) |
|---|---|---|
| Coloring | 8 | 10 |
| Acidity (%) | 0.004 | 0.086 |

In storage, samples taken at pipe (32) colored very slowly.

EXAMPLE 10

The following examples better illustrate the processing of resin-treated isophorone. This processing serves to minimize the acidity of the final product. A discoloration reactor consists of a stainless steel cylinder thermostatically controlled at 100° C. The reactor is charged with a half liter of dried "Amberlyst 15" I.G. ion-exchanging resin. Then the reactor is supplied with tailed, topped and dried isophorone at a flow rate of 500 ml/hr. The reactor runs at atmospheric pressure.

The reactor effluent possesses a dark brown color. The acidity of the effluent is 0.029% expressed in terms of acetic acid. The acidity was measured by adding 0.1 N alcoholic potash to a 50 ml sample of diluted colorless isophorone in the presence of thymol blue.

Four liters of this effluent kept at 80° C. are added to 44 ml of a 20 g/l aqueous solution of sodium hydroxide. The neutralized mixture is agitated for 15 minutes. At the end of that period, 9.5 ml of a 10 g/l aqueous solution of phosphoric acid and 1 liter of double distilled water are introduced into the agitated alkaline mixture. The organic layer is then separated from the lower aqueous layer. The organic layer is dried by heterodistillation before introduction into the middle of a continuous distillation column. The column has a diameter of 50 mm, and 16 theoretical plates. The column working conditions are as follows:

| Pressure | 50 mm of mercury |
|---|---|
| Head temperature | 119° C. |
| Foot temperature | 126° C. |
| Feeding throughput rate | 1 l/hr |
| Flow throughput rate at the head | 940 ml/hr |
| Rate of reflux | 2/1 |
| Drawing-off rate at the foot | 60 ml/hr |

Isophorone flowing at the column head had the following characteristics after 4 hours:
Coloring—8
Acidity—0.0018%

EXAMPLE 11

Utilizing the apparatus as operated in Example 10, the average sample acidity was 0.06% after 10 hours treatment.

Four liters of the above samples are added to 92 ml of an agitated aqueous solution of sodium hydroxide. The alkaline solution has a concentration of 20 g of soda per liter and is maintained at 80° C. After 15 minutes of agitation, 20 ml of a 10 g/l aqueous solution of phosphoric acid and 1 liter of double distilled water are introduced.

The organic layer is separated from the aqueous layer and dried by means of heterodistillation. The organic layer is then introduced into a distillation column, identical to the one described in Example 10.

Isophorone flowing the column head has the following characteristics:
Coloring—8
Acidity—0.0015%

The samples were preserved in closed opaque glass bottles for 40 days. At the end of that period of time, the following characteristics were obtained:
Coloring—15
Acidity—0.0031%

We claim:
1. A process for removing color and stabilizing isophorone characterized by:
(1) distilling a raw synthesis mixture to remove alkaline agents, acetone, and a major portion of the water which is present;
(2) thermally and catalytically treating the distilled isophorone containing mixture with an acidic ion-exchange resin;
(3) treating the effluent resulting from the thermal and catalytic treatment with an excess of an alkaline agent;
(4) neutralizing the excess alkaline in the mixture wherein the pH of the resultant mixture is between about 6.5 and 7;
(5) washing the effluent with water in a volume sufficient to dissolve salts formed by the addition of the alkaline agent;
(6) separating the resulting aqueous layer to provide an organic mixture layer of less than about 1% water content;
(7) distilling the organic mixture under reduced pressure; and
(8) recovering colorless and stable isophorone.

2. The process as recited in claim 1 wherein the thermal catalytic treatment is carried out at a temperature etween about 80° C. and 120° C.

3. The process recited in claim 1 wherein the crude synthesis mixture is retained on the ion-exchange resin for between about 30 minutes and about 4 hours.

4. The process recited in claim 1 wherein the ion-exchange resin is of the macroporous type.

5. The process recited in claim 4 wherein the ion-exchange resin is characterized by balls in the dry state having an apparent diameter between 0.3 mm and 1.5 mm; and a porosity between 0.3 mm and 1.5 mm; a porosity between 25% and 45%; a BET specific surface between 20 m²/g and 50 m²/g; and macropores with diameters greater than 100 Å.

6. The process recited in claim 1 wherein the raw synthesis mixture is derived from the alkaline condensation of acetone at a high temperature.

7. The process recited in claim 1 wherein the alkaline addition to the isophorone is characterized by the addition of a 15% stoichiometric excess of an aqueous solution of sodium hydroxide whose concentration lies between 10 and 30 g/l.

8. The process recited in claim 1 wherein the neutralization of the alkaline mixture is characterized by the addition of a 10 g/l aqueous solution of phosphoric acid.

9. The process recited in claim 1 wherein the washing of the mixture is characterized by the addition of a volume of water equal to one fourth the volume of the organic product.

10. The process recited in claim 1 wherein the distillation of the washed isophorone mixture is characterized by a heteroazeotropic drying and a subsequent distillation.

* * * * *

UNITED STATES PATENT AND TRADEMARK OFFICE
CERTIFICATE OF CORRECTION

PATENT NO. : 4,248,673
DATED : February 3, 1981
INVENTOR(S) : Bernard Cheminal and Paul Kiener It is certified that error appears in the above—identified patent and that said Letters Patent is hereby corrected as shown below:

Column 7, line 62, Table. Allignment should be corrected by placing "< 5" under table columns 3.3 and 5.3 and the words "Not measured" under table column 9.

Column 11, line 18, reads "21", should read --2/1--

Signed and Sealed this

Sixteenth Day of June 1981

[SEAL]

Attest:

RENE D. TEGTMEYER

Attesting Officer     Acting Commissioner of Patents and Trademarks